US00PP25485P2

(12) United States Plant Patent
Lander et al.

(10) Patent No.: US PP25,485 P2
(45) Date of Patent: Apr. 28, 2015

(54) ***PETUNIA* PLANT NAMED 'KL 1117'**

(50) Latin Name: *Petunia×hybrida*
Varietal Denomination: KL 1117

(71) Applicants: Ken Lander, Pugwash (CA); Mary Maxine Johnson, Pugwash (CA)

(72) Inventors: Ken Lander, Pugwash (CA); Mary Maxine Johnson, Pugwash (CA)

(73) Assignee: Mary Maxine Johnson, Pugwash, Nova Scotia (CA)

( * ) Notice: Subject to any disclaimer, the term of this patent is extended or adjusted under 35 U.S.C. 154(b) by 108 days.

(21) Appl. No.: 13/986,658

(22) Filed: May 21, 2013

(51) Int. Cl.
*A01H 5/00* (2006.01)

(52) U.S. Cl.
USPC ..... Plt./356.15

(58) Field of Classification Search
USPC ..... Plt./356.1, 356.15
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'KL 1117', characterized by its outwardly spreading, mounding and cascading plant habit; freely branching and vigorous growth habit; early and freely flowering habit; large single flowers that are white in color; and good garden performance.

1 Drawing Sheet

Botanical designation: *Petunia×hybrida*.
Cultivar denomination: 'KL 1117'.

BACKGROUND OF THE INVENTION

The present invention relates to a new and distinct cultivar of *Petunia* plant, botanically known as *Petunia×hybrida* and hereinafter referred to by the name 'KL 1117'.

The new *Petunia* plant is a naturally-occurring branch mutation of *Petunia×hybrida* 'Lavender Skies', disclosed in U.S. Plant Pat. No. 21,692. The new *Petunia* was discovered and selected by the Inventors on a single flowering plant from within a population of plants of 'Lavender Skies' in a controlled greenhouse environment in Pugwash, Nova Scotia, Canada in May, 2010. Asexual reproduction of the new *Petunia* plant by vegetative cuttings in a controlled greenhouse environment in Pugwash, Nova Scotia, Canada since May, 2010, has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'KL 1117'. These characteristics in combination distinguish 'KL 1117' as a new and distinct *Petunia* plant:

1. Outwardly spreading, mounding and cascading plant habit.
2. Freely branching and vigorous growth habit.
3. Early and freely flowering habit.
4. Large single flowers that are white in color.
5. Good garden performance.

Plants of the new *Petunia* differ from plants of the mutation parent, 'Lavender Skies', primarily in flower color as plants of 'Lavender Skies' have purple violet-colored flowers.

Plants of the new *Petunia* can be compared to plants of 'Kakegawa S30', disclosed in U.S. Plant Pat. No. 13,862. In side-by-side comparisons, plants of the new *Petunia* differed from plants of 'Kakegawa S30' in the following characteristics:

1. Plants of the new *Petunia* were taller and more vigorous than plants of 'Kakegawa S30'.
2. Plants of the new *Petunia* were more mounding than and not as flat as plants of 'Kakegawa S30'.
3. Plants of the new *Petunia* and 'Kakegawa S30' differed in flower throat color.

Plants of the new *Petunia* can also be compared to plants of 'Conbloss', disclosed in U.S. Plant Pat. No. 13,556. In side-by-side comparisons, plants of the new *Petunia* differed from plants of 'Conbloss' in the following characteristics:

1. Plants of the new *Petunia* were more vigorous than plants of 'Conbloss'.
2. Plants of the new *Petunia* were more mounding than and not as trailing as plants of 'Conbloss'.
3. Plants of the new *Petunia* had larger flowers than plants of 'Conbloss'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'KL 1117' grown in a container.

The photograph at the top of the sheet is a close-up view of a typical flowering plant of 'KL 1117'.

DETAILED BOTANICAL DESCRIPTION

The aforementioned photographs and following observations, measurements and values describe plants grown during the autumn in one-gallon containers an outdoor nursery in Bonsall, Calif. and under cultural practices typical of commercial *Petunia* production. During the production of the plants, day temperatures ranged from 18° C. to 38° C., night temperatures ranged from 9° C. to 18° C. and light levels ranging from 7,000 to 10,000 foot-candles. Plants were pinched one time and were three months old when the photographs and description were taken. In the following description, color references are made to The Royal Horticultural Society Colour Chart, 2007 Edition, except where general terms of ordinary dictionary significance are used.

Botanical classification: *Petunia×hybrida* 'KL 1117'.

Parentage: Naturally-occurring branch mutation of *Petunia×hybrida* 'Lavender Skies', disclosed in U.S. Plant Pat. No. 21,692.

Propagation:

*Type*.—Terminal vegetative cuttings.

*Time to initiate roots, summer and winter*.—About 10 days at 21° C.

*Time to produce a rooted young plant, summer*.—About 17 days at 21° C.

*Time to produce a rooted young plant, winter*.—About 27 days at 21° C.

*Root description*.—Medium in thickness, fibrous; white in color.

*Rooting habit*.—Freely branching; medium density.

Plant description:

*Plant and growth habit*.—Outwardly spreading, mounding and cascading plant habit with about eight primary lateral branches with multiple secondary lateral branches developing per plant; dense and bushy appearance; pinching enhances development of lateral branches; vigorous growth habit.

*Plant height*.—About 22 cm.

*Plant diameter* (*area of spread*).—About 30 cm by 34 cm.

*Lateral branches*.—Length: About 34 cm. Diameter: About 3 mm. Internode length: About 2.4 cm. Aspect: Initially upright then falling outwardly to trailing. Texture: Pubescent. Color: Close to 146B.

Leaf description:

*Arrangement*.—Alternate before flowering; opposite after flowers develop; simple.

*Length*.—About 5 cm.

*Width*.—About 2.9 cm.

*Shape*.—Elliptical to slightly ovate.

*Apex*.—Acute.

*Base*.—Attenuate.

*Margin*.—Entire.

*Texture, upper and lower surfaces*.—Pubescent.

*Venation pattern*.—Pinnate, arcuate.

*Color*.—Developing leaves, upper surface: Close to 138A. Developing leaves, lower surface: Close to 146B. Fully expanded leaves, upper surface: Close to 137B; venation, close to 146B. Fully expanded leaves, lower surface: Close to 146B; venation, close to 147C.

*Petioles*.—Length: About 6 mm. Diameter: About 4 mm. Texture, upper and lower surfaces: Scattered pubescence. Color, upper and lower surfaces: Close to 146D.

Flower description:

*Flower type and flowering habit*.—Single axillary salverform flowers; flowers face mostly upright; freely flowering habit with about ten to twelve flowers developing per lateral branch and more than 100 flowers potentially developing per plant.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About three to four days; flowers persistent.

*Fragrance*.—None detected.

*Flower buds*.—Length: About 4.4 cm. Diameter: About 7 mm. Shape: Oblong. Color: Close to 145D.

*Flower diameter*.—About 4.5 cm.

*Flower depth* (*height*).—About 5.3 cm.

*Throat diameter, distal*.—About 8 mm.

*Tube length*.—About 3.9 cm.

*Tube diameter, proximal*.—About 5 mm.

*Petals*.—Quantity and arrangement: Five petals fused in a single salverform whorl. Petal lobe length (from throat): About 2 cm. Petal lobe width: About 2.4 cm. Petal lobe shape: Obovate. Petal lobe apex: Nearly round to slightly emarginate. Petal lobe margin: Entire. Petal lobe texture, upper and lower surfaces: Smooth, glabrous. Throat texture: Smooth, glabrous. Tube texture: Pubescent. Color: When opening, upper surface: Close to NN155D. When opening, lower surface: Close to 157D. Fully opened, upper surface: Close to NN155D; venation, close to 145C; color does not change or shift with development. Fully opened, lower surface: Close to NN155D; venation, close to 145B; color does not change or shift with development. Flower throat (inside): Close to 145C; venation, close to N144D. Flower tube (outside): Close to 145D; venation, close to N144D.

*Sepals*.—Quantity and arrangement: Five sepals fused in a single star-shaped whorl. Length: About 1.9 cm. Width: About 3 mm. Shape: Lanceolate. Apex: Rounded to slightly acute. Margin: Entire. Texture, upper and lower surfaces: Pubescent; minute. Color, upper and lower surfaces: Close to 146A.

*Peduncles*.—Length: About 2.7 cm. Width: About 1 mm. Angle: About 35° to 45° from the stem axis. Strength: Strong. Texture: Pubescent; minute. Color: Close to 145A.

*Reproductive organs*.—Stamens: Quantity per flower: Five. Filament length: About 2 cm. Filament color: Close to 145D. Anther length: About 1.5 mm. Anther shape: Oval. Anther color: Close to 196B. Pollen amount: Scarce. Pollen color: Close to 198D. Pistils: Quantity per flower: One. Pistil length: About 2.5 cm. Style length: About 2.1 cm. Style color: Close to 145D. Stigma shape: Round. Stigma color: Close to 144C. Ovary color: Close to 145A.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'KL 1117' as illustrated and described.

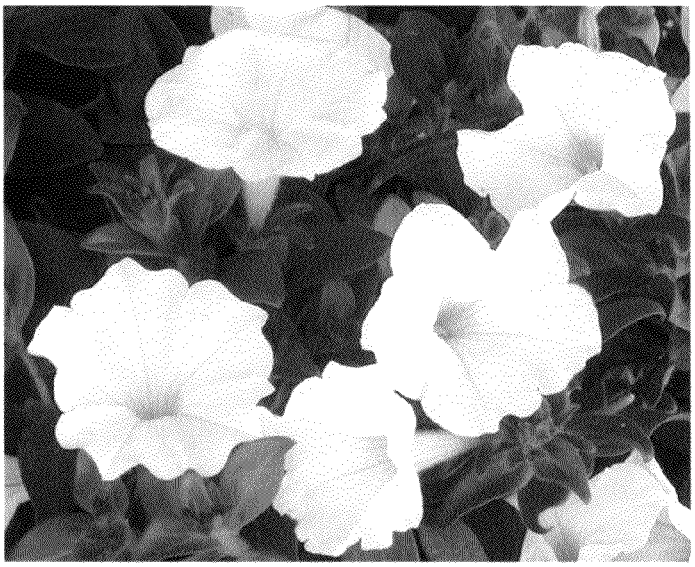
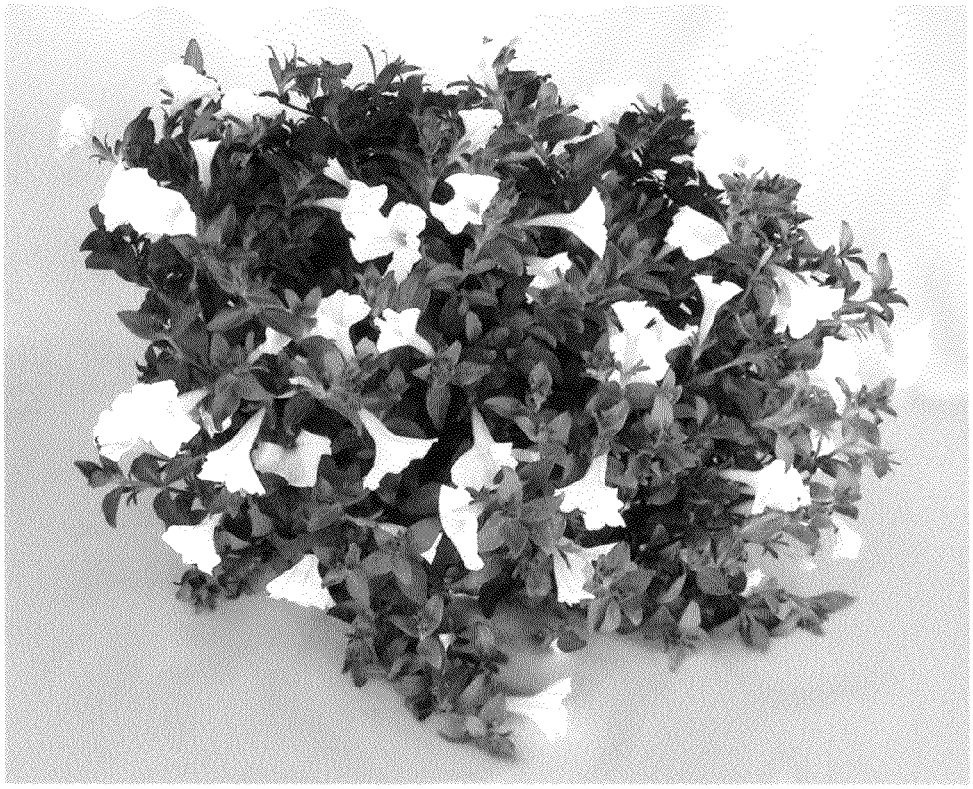

* * * * *